(12) United States Patent
Igarashi

(10) Patent No.: US 12,618,041 B2
(45) Date of Patent: May 5, 2026

(54) CELL CULTURING SYSTEM

(71) Applicant: Terumo Kabushiki Kaisha, Tokyo (JP)

(72) Inventor: Masatsugu Igarashi, Kanagwa (JP)

(73) Assignee: Terumo Kabushiki Kaisha (JP)

( * ) Notice: Subject to any disclaimer, the term of this patent is extended or adjusted under 35 U.S.C. 154(b) by 536 days.

(21) Appl. No.: 18/205,270

(22) Filed: Jun. 2, 2023

(65) Prior Publication Data

US 2023/0303960 A1 Sep. 28, 2023

Related U.S. Application Data

(63) Continuation of application No. PCT/JP2021/046188, filed on Dec. 15, 2021.

(30) Foreign Application Priority Data

Dec. 24, 2020 (JP) ................................. 2020-214579

(51) Int. Cl.
*C12M 1/34* (2006.01)
*C12M 1/36* (2006.01)

(52) U.S. Cl.
CPC ............ *C12M 41/36* (2013.01); *C12M 41/48* (2013.01)

(58) Field of Classification Search
CPC .............................. C12M 41/36; C12M 41/48
See application file for complete search history.

(56) References Cited

U.S. PATENT DOCUMENTS

2017/0191019 A1 7/2017 Kawarai et al.
2019/0302006 A1 10/2019 Kono et al.

FOREIGN PATENT DOCUMENTS

| DE | 102017216402 A1 | | 3/2019 |
|----|------|---|--------|
| EP | 3045521 A1 | | 7/2016 |
| FR | 2637083 A1 | | 3/1990 |
| JP | 2002243632 A | * | 8/2002 |
| JP | 2017143775 A | | 8/2017 |
| JP | 2019-174338 A | | 10/2019 |

(Continued)

OTHER PUBLICATIONS

Written Opinion of the International Searching Authority dated Apr. 7, 2022, issued in corresponding PCT Application No. PCT/JP2021/046188 (6 pages).

(Continued)

*Primary Examiner* — Liban M Hassan

(74) *Attorney, Agent, or Firm* — Harness, Dickey & Pierce, P.L.C.

(57) ABSTRACT

A cell culturing system is equipped with a reactor, a flow path through which a culture medium flows into and flows out from the reactor, an optical measurement unit that optically measures cells contained in the culture medium, and a control unit that processes measurement results of the optical measurement unit. The optical measurement unit includes, at different positions in a flow direction of the culture medium, a first measurement unit that performs optical measurements based on of emission a first measurement light, and a second measurement unit that performs optical measurements based on emission of a second measurement light. In addition, a first optical path length of the first measurement light is set to be longer than a second optical path length of the second measurement light.

14 Claims, 6 Drawing Sheets

(56)　　　　　References Cited

FOREIGN PATENT DOCUMENTS

| JP | 2020156371 | A | 10/2020 |
| WO | 2016-013395 | A1 | 1/2016 |
| WO | 2021094009 | A1 | 5/2021 |

OTHER PUBLICATIONS

Office Action for corresponding Japanese Patent Application No. 2023-525488 dated Sep. 18, 2025 (4 pgs).
International Search Report dated Apr. 7, 2022, issued in corresponding PCT Application No. PCT/JP2021/046188 (4 pages).

* cited by examiner

10(24)

FIG. 3A
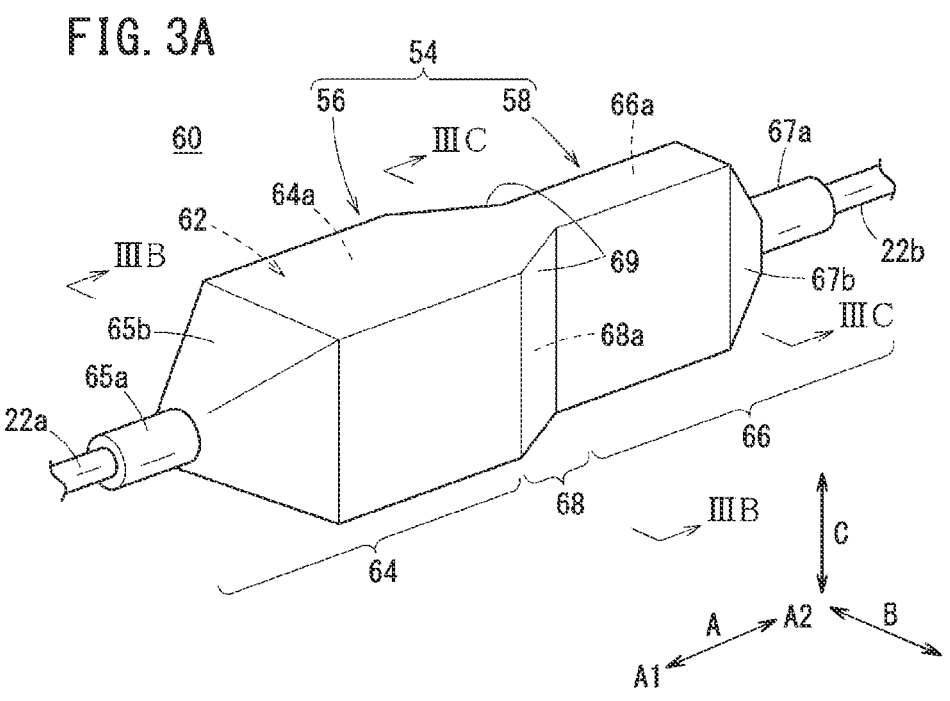
FIG. 3B
FIG. 3C
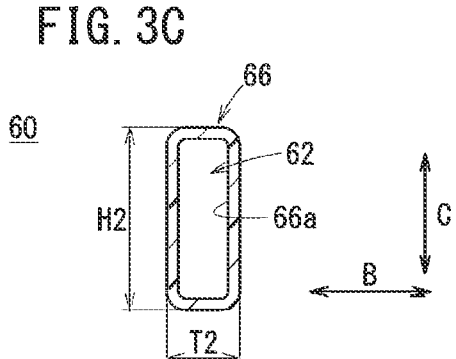

FIG. 6

CELL CULTURING SYSTEM

CROSS-REFERENCED TO RELATED APPLICATIONS

The present application is a continuation application of the International Patent Application No. PCT/JP2021/046188 filed on Dec. 15, 2021, which designated the U.S. and claims the benefit of priority from Japanese Patent Application No. JP2020-214579 filed Dec. 24, 2020. The entire disclosures of the above-identified applications are incorporated herein by reference.

FIELD

The present disclosure relates to a cell culturing system that is used to measure a number of cells flowing from a reactor.

BACKGROUND

In the practice of regenerative medicine, a treatment may be performed in which biological cells are collected and cultured, and the cultured cells may be administered to a patient. In a cell culturing process for culturing cells, for example, as disclosed in JP 2017-143775 A, a cell culturing system may be used that has a cell culturing container (e.g., reactor)) that includes hollow fibers disposed in an interior of a case. In such a cell culturing system, culturing of cells may be carried out by seeding the cells in the hollow fibers of the reactor, and thereafter, a culture medium may be delivered into the reactor via a flow path connected to the reactor.

In this type of cell culturing system, in order to grasp the state of the cell culture and determine the timing at which the cells are collected, it is important to accurately monitor the number of cells that are propagated during culturing. Although it is a general practice to aseptically collect the culture medium inside the cell culturing system through an aseptic filter, the cells are incapable of passing through aseptic filters. For this reason, the culture medium is often collected in an aseptic manner, and the concentration of metabolites of the cells (such as lactic acid, glucose, and oxygen) within the culture medium is measured, and used to indirectly calculate the number of cells that were propagated. Further, as a method of aseptically collecting the cells directly, a circuit tube of the cell culturing system may be sealed over a certain length, and a piece of the tube including the cell-containing culture medium may be collected. Thereafter, the disconnected circuit of the cell culturing system may be connected again using an aseptic joining device.

In the instance of indirectly calculating the number of cells as a result of changes in the culturing environment, the cell metabolism can undergo changes and an accurate measurement of the number of cells often cannot be performed. Further, in the case of collecting the tube in which cell-containing culture medium is included, the operation often becomes complicated, and moreover the culturing operation must be temporarily interrupted, such that cells are lost at the time of sampling.

SUMMARY

The present disclosure provides a cell culturing system in which it is possible to continuously measure the number of cells in a reactor in a state in which sterility is assured and where a sufficient degree of measurement accuracy can be obtained.

A cell culturing system according to the present disclosure includes a reactor configured to culture cells based on a culture medium that flows therethrough, a flow path through which the culture medium flows into and flows out from the reactor, an optical measurement unit disposed in the flow path downstream of the reactor in a flow direction of the culture medium, and a processing unit that may be configured to process a measurement result of the optical measurement unit. The optical measurement unit may be configured to irradiate the culture medium with measurement light and thereby to optically measure a state of the culture medium. The optical measurement unit may include a first measurement unit and a second measurement unit arranged at different positions in the flow direction of the culture medium. The first measurement unit may include a first optical path section through which the culture medium flows together with first measurement light being transmitted therein. The second measurement unit ay include a second optical path section through which the culture medium flows together with second measurement light being transmitted therein. A first optical path length of the first optical path section may be longer than a second optical path length of the second optical path section.

The cell culturing system may be configured to continuously measure the number of cells in the reactor in a state in which sterility is assured and where a sufficient degree of measurement accuracy can be obtained.

BRIEF DESCRIPTION OF THE DRAWINGS

FIG. 3A is a perspective view illustrating a measurement container of an optical measurement unit for use with the example cell culturing system illustrated in FIG. 1;

FIG. 3B is a cross-sectional view taken along line IIIB-IIIB of FIG. 3A;

FIG. 3C is a cross-sectional view taken along line IIIC-IIIC of FIG. 3A;

FIG. 6 is a partial cross-sectional view illustrating another example optical measurement unit for use with the example cell culturing system illustrated in FIG. 1.

DETAILED DESCRIPTION

Preferred embodiments of the present disclosure will be presented and described in detail below with reference to the accompanying drawings.

Figure 1:
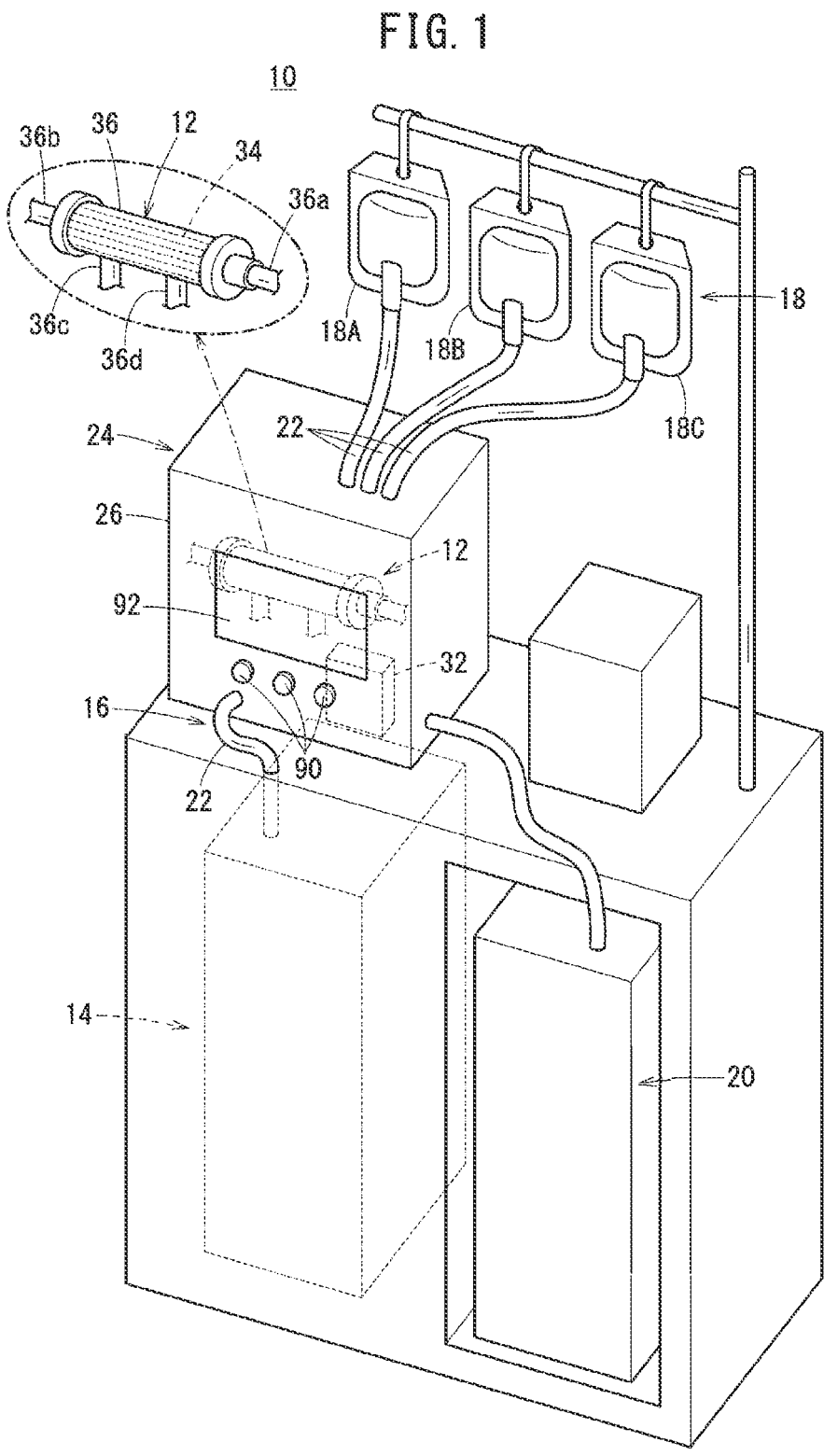
FIG. 1 is a perspective view illustrating a structure of an example cell culturing system according to at least one example embodiment of the present disclosure.

A cell culturing system 10 according to at least one example embodiment of the present invention is illustrated in FIG. 1. The cell culturing system 10 may be configured as a stationary device that is installed in a sterile room (or the like) and to carry out a culturing process for culturing biological cells in the practice of regenerative medicine. The cell culturing system 10 may be equipped with a reactor 12 that is configured to serve as a cell culturing container. The cell culturing system 10 may continue with the culturing of cells over a prolonged period of time, by supplying a culture medium and oxygen to the reactor 12, and discharging from the reactor 12 unused culture medium, oxygen, lactic acid, carbon dioxide, and/or the like that may be generated during the culturing of cells.

The cells of a biological body are not particularly limited, and may include, for example, cells (e.g., T cells and the like) contained in blood and/or stem cells (e.g., ES cells, iPS cells, mesenchymal stem cells, and the like). An appropriate culture medium may be selected according to the biological cells. A culture medium may include a balanced salt solution (BSS) as a basic solution. Various amino acids, vitamins, serum, and the like may be added to the basic solution to prepare the culture medium.

The cell culturing system 10 may include a culture medium storage unit 14 in which the culture medium is stored, a flow path 16 disposed between the reactor 12 and the culture medium storage unit 14, a plurality of medical bags 18 connected to the flow path 16, and a waste liquid unit 20 in which the liquid discharged from the flow path 16 may be stored. Although the cell culturing system 10 is illustrated as including a single reactor 12, it should be appreciated that, in certain variations, the cell culturing system 10 may be configured to be equipped with a plurality of reactors 12.

In the culture medium storage unit 14 may include a hard tank capable of storing a large amount of the culture medium and may be configured to supply the culture medium to the reactor 12. For example, in certain variations, the hard tank may be configured to hold a volume on the order of 5 L to 30 L. Because of the size of the hard tank, a workload of frequently replacing the culture medium storage unit 14 during the culturing process may be reduced. Moreover, concerning the culture medium storage unit 14, a flexible medical bag or the like may be applied thereto.

The flow path 16 may include a plurality of tubes 22 (in FIG. 1, only one of the tubes 22 which is connected to the culture medium storage unit 14 is shown). The plurality of tubes 22 may be connected to the culture medium storage unit 14 and the plurality of medical bags 18, together with being connected to the reactor 12. The cell culturing system 10 may be configured to supply and discharge the culture medium in the culture medium storage unit 14 and the liquids in the medical bags 18 to the reactor 12 via the plurality of tubes 22.

The plurality of medical bags 18 may include, for example, a cell solution bag 18A in which a liquid (e.g., cell solution) containing cells is stored, a cleaning solution bag 18B in which a cleaning solution is stored, a stripping solution bag 18C in which a stripping solution is stored, and a non-illustrated collection bag in which cultured cells are collected. The cleaning solution may be a liquid that is used when priming the reactor 12 and the flow path 16. For example, the cleaning solution may include buffering solutions, such as PBS (Phosphate Buffered Salts), TBS (Tris-Buffered Saline), and/or the like, and/or physiological saline. The stripping solution may be a liquid that strips or peels off the cells which have been cultured by the culturing process. As the stripping solution, for example, trypsin or an EDTA solution can be applied thereto.

When the cell culturing system 10 is constructed, the flow path 16 may be set in a manner so as to pass through a flow path control mechanism 24. The flow path control mechanism 24 may be equipped with an enclosure 26 in which a portion of the flow path 16 is accommodated. Further, the flow path control mechanism 24 may be provided in the interior of the enclosure 26 with clamps 28 for opening and closing predetermined tubes 22, pumps 30 for allowing the liquid inside the tubes 22 to flow, and/or a control unit 32 that controls the operation of the clamps 28 and the pumps 30 (refer to FIG. 2). More specifically, in the interior of the enclosure 26, by opening and closing the clamps 28, the flow path control mechanism 24 may selectively switch the tubes 22 through which the liquid flows allowing the liquid in the flow path 16 to flow under the operation of the pumps 30.

Apart from the plurality of tubes 22, the flow path 16 may be equipped with a cassette (not shown) having a plurality of liquid flow paths, and to which several of the tubes 22 may be connected. In this case, the cassette may be arranged on the clamps 28 of the flow path control mechanism 24 accompanying setting of the cassette inside the enclosure 26, and the flow paths inside the cassette may be opened and closed or switched by the clamps 28.

Concerning the reactor 12 that may be connected to the flow path 16, in order to widen the area over which culturing is carried out, a structure including hollow fibers 34 may be preferably applied thereto. More specifically, the reactor 12 may include a plurality of (for example, 10,000 or more) hollow fibers 34, and a case 36 in which the plurality of hollow fibers 34 are accommodated along an axial direction thereof.

The respective hollow fibers 34 may include non-illustrated cavities that penetrate along the direction of extension thereof, and the cells may be seeded on inner peripheral surfaces that constitute the internal cavities. Further, the respective hollow fibers 34 may include a plurality of non-illustrated pores communicating between an outer side and the internal cavities, and the respective pores may allow solutions or substances of low molecular weight to pass, without allowing cells or proteins to pass therethrough. Consequently, the culture medium, and a predetermined gas component or the like may be supplied via the pores to the cells on the inner peripheral surfaces of the hollow fibers 34. Hereinafter, a configuration in which liquid primarily flows in the internal cavities of the hollow fibers 34 may also be referred to as an IC (intra capillary) configuration, and a configuration in which liquid primarily flows on an outer side of the hollow fibers 34 may also be referred to as an EC (extra capillary) configuration.

The material constituting the hollow fibers 34 is not particularly limited. In certain variations, the hollow fibers 34 include polyolefin may resins (such as polypropylene, polyethylene, and/or the like) and/or polymer materials (such as polysulfone, polyether sulfone, polyacrylonitrile, polytetrafluoroethylene, polystyrene, polymethylmethacrylate, cellulose acetate, cellulose triacetate, regenerated cellulose, and/or the like).

The case 36 may be formed in a cylindrical shape and possesses rigidity. The case 36 may be equipped with a first IC terminal 36a, a second IC terminal 36b, a first EC terminal 36c, and/or a second EC terminal 36d that are connected to the plurality of tubes 22. The first IC terminal 36a may be provided at one end in the axial direction of the case 36, and may communicate with the internal cavities of the hollow fibers 34. The second IC terminal 36b may be provided at another end in the axial direction of the case 36, and may communicate with the internal cavities of the hollow fibers 34. The first EC terminal 36c may be provided in proximity to the other end on a side surface of the case 36, and may communicate with a space on the outer side of the hollow fibers 34 in the interior of the case 36. The second EC terminal 36*d* may be provided in proximity to the one end on the side surface of the case 36, and may communicate with the space on the outer side of the hollow fibers 34 in the interior of the case 36.

Hereinafter, with reference to FIG. 2, a description will be given in detail concerning the configuration of the flow path 16 between the reactor 12 and the culture medium storage unit 14, and the flow path control mechanism 24.

The flow path 16 may include a culture medium delivery route 40 connected to the culture medium storage unit 14, and an IC route 42 (internal route) and an EC route 44 (external route) branching off from the culture medium delivery route 40. The IC route 42 may be a pathway for supplying liquids to the internal cavities of the hollow fibers 34. The EC route 44 may be a pathway for supplying liquids to the interior of the case 36 on an outer side of the hollow fibers 34.

A first clamp 40*a* that opens or interrupts the supply of the culture medium from the culture medium storage unit 14 may be disposed in the culture medium delivery route 40.

The IC route 42 may include an IC circulation circuit 42*a* which is capable of circulating liquid between the reactor 12, and an IC supply circuit 42*b* which is capable of allowing liquid to flow from the culture medium delivery route 40 to the IC circulation circuit 42*a*. An IC circulation pump 30*a* that causes the liquid to circulate may be provided in the IC circulation circuit 42*a*. An IC supply pump 30*b* that causes the liquid to flow from the culture medium delivery route 40 to the IC circulation circuit 42*a* may be provided in the IC supply circuit 42*b*. Further, although not illustrated, in the IC supply circuit 42*b*, in addition to the culture medium storage unit 14, the plurality of medical bags 18 (e.g., the cell solution bag 18A, the cleaning solution bag 18B, and/or the stripping solution bag 18C) may be connected via the plurality of tubes 22. Further, the medical bags 18 may be replaced with collection bags or the like using an aseptic joining device for aseptically joining the bags depending on the intended use thereof.

The IC circulation circuit 42*a* may be connected to the first IC terminal 36*a* and the second IC terminal 36*b* of the reactor 12. Accordingly, the liquid circulating in the IC circulation circuit 42*a* may flow through the internal cavities of the hollow fibers 34 under the operation of the IC circulation pump 30*a*. In the IC circulation circuit 42*a*, an IC waste liquid circuit 46 may be connected to a more downstream side than the reactor 12. A second clamp 46*a* that opens or interrupts discharging of the liquid from the IC circulation circuit 42*a* may be provided in the IC waste liquid circuit 46. The IC waste liquid circuit 46 may be connected to a merging route 50, and the culture medium flowing through the IC waste liquid circuit 46 may be discharged to the waste liquid unit 20 via the tubes 22 of the merging route 50.

In addition, the IC circulation circuit 42*a* may include an optical measurement unit 54 on a more downstream side in the flow direction of the liquid than the reactor 12 (e.g., between the reactor 12 and the IC waste liquid circuit 46). The optical measurement unit 54 may be configured to perform an optical measurement with respect to the culture medium flowing out from the internal cavities of the hollow fibers 34 and to transmit the measurement result to the control unit 32. On the basis of the measurement result, the control unit 32 may manage the number of cells within the culture medium by calculating the number of cells contained in the culture medium. A specific configuration of the optical measurement unit 54 will be described in detail later.

On the other hand, the EC route 44 may include an EC circulation circuit 44*a* that is capable of circulating liquid between the reactor 12 and an EC supply circuit 44*b* that is capable of allowing liquid to flow from the culture medium delivery route 40 to the EC circulation circuit 44*a*. An EC circulation pump 30*c* that causes the liquid to circulate may be provided in the EC circulation circuit 44*a*. An EC supply pump 30*d* that causes the liquid to flow from the culture medium delivery route 40 to the EC circulation circuit 44*a* may be provided in the EC supply circuit 44*b*. Further, although not illustrated, in the EC supply circuit 44*b*, in addition to the culture medium storage unit 14, the plurality of medical bags 18 (the cleaning solution bag 18B and the stripping solution bag 18C) may be connected via the plurality of tubes 22.

The EC circulation circuit 44*a* may be connected to the first EC terminal 36*c* and the second EC terminal 36*d* of the reactor 12. Accordingly, the liquid circulating in the EC circulation circuit 44*a* flows through the interior of the case 36 under the operation of the EC circulation pump 30*c*. A gas exchanger 52 may be provided on an upstream side of the reactor 12 in the EC circulation circuit 44*a*. The gas exchanger 52 may discharge carbon dioxide that is mixed in the culture medium, while on the other hand, mixes predetermined gas components (nitrogen $N_2$: 75%, oxygen $O_2$: 20%, carbon dioxide $CO_2$: 5%) into the culture medium. The structure of the gas exchanger 52 is not particularly limited, and for example, similar to that of the reactor 12, a structure can be applied in which a plurality of hollow fibers are provided inside a case.

In the EC circulation circuit 44*a*, an EC waste liquid circuit 48 may be connected downstream of the reactor 12. A third clamp 48*a* that opens or interrupts discharging of the liquid from the EC circulation circuit 44*a* may be provided in the EC waste liquid circuit 48. The EC waste liquid circuit 48 may be connected to the merging route 50, and the culture medium flowing through the EC waste liquid circuit 48 may be discharged to the waste liquid unit 20 via the tubes 22 of the merging route 50.

Further, as discussed above, in the case that a plurality (e.g., five) of the reactors 12 are provided, the cell culturing system 10 may be configured to include a plurality of the IC circulation circuits 42*a* and the EC circulation circuits 44*a* corresponding to each of the reactors 12. Stated d otherwise, other non-illustrated IC circulation circuits and EC circulation circuits, through which liquid is caused to circulate in other reactors 12, may be connected in parallel to a branching point X between the IC supply pump 30*b* and the IC circulation circuits 42*a*, and a branching point Y between the EC supply pump 30*d* and the EC circulation circuits 44*a*.

Next, a description will be given concerning the optical measurement unit 54 provided in the IC circulation circuit 42*a*. The optical measurement unit 54 measures, by way of a turbidity method, the number of cells contained in the culture medium on the downstream side of the reactor 12. Further, the optical measurement unit 54 may include, at different positions in the flow direction of the culture medium, a first measurement unit 56 that performs optical measurements based on emission of a first measurement light L1, and a second measurement unit 58 that performs optical measurements based on emission of a second measurement light L2.

In addition, the flow path 16 may include, as the configuration of the optical measurement unit 54, a measurement container 60 arranged in the first measurement unit 56 and the second measurement unit 58. On the other hand, the flow path control mechanism 24 may include, as the configuration of the optical measurement unit 54, a first measurement structure 70 disposed in the first measurement unit 56, and a second measurement structure 71 disposed in the second measurement unit 58.

As shown in FIGS. 3A to 3C, the measurement container 60 may be connected to the tubes 22 (e.g., an upstream side tube 22a and a downstream side tube 22b) that make up the IC circulation circuit 42a. The measurement container 60 maty extend in a linear shape and may be formed in a square tube shape that is thicker than the tubes 22. A passage 62 through which the culture medium flows may be provided in the interior of the measurement container 60. The passage 62 may extend along the axial direction of the measurement container 60 (e.g., in the direction of the arrow A shown in FIG. 3A) and may communicates with the flow path in the upstream side tube 22a and the flow path in the downstream side tube 22b.

The measurement container 60 may be formed to be colorlessly transparent or translucent in order for the first measurement light L1 and the second measurement light L2 to be capable of passing therethrough. The measurement container 60 may be formed to be harder (e.g., with a higher modulus of elasticity) than the tubes 22 which possess flexibility and may be configured in a manner so as not to undergo elastic deformation when arranged in the optical measurement unit 54. Moreover, the measurement container 60 may have a softness that is capable of being elastically deformed, so as to be brought into intimate contact with respect to the first measurement structure 70 and the second measurement structure 71. The shape of the measurement container 60 is not limited to being a square tube shape, and for example, may be a cylindrical shape or a disk-like shape.

The measurement container 60 may include a plurality of measurement cells (e.g., a first cell 64 and a second cell 66) along the axial direction. The first cell 64 may be formed in a range from a substantially intermediate position in the axial direction to one end side (e.g., the side of the arrow A1) of the measurement container 60, and the second cell 66 may be formed in a range from a substantially intermediate position in the axial direction to another end side (e.g., the side of the arrow A2) of the measurement container 60. An axial length of the first cell 64 and an axial length of the second cell 66 may be set to be approximately the same as each other.

The first cell 64 may be formed so as to possess a relatively large flow path cross-sectional area and volume. The first cell 64 may exhibit a substantially rectangular-like shape as viewed in cross-section perpendicular to the axial direction of the measurement container 60, and a thickness T1 thereof along a direction (i.e., thickness direction) of the arrow B shown in FIG. 3B is substantially equivalent to a height H1 thereof along a direction (i.e., height direction) of the arrow C shown in FIG. 3B.

In accordance with the shape of the container of the first cell 64, a first space 64a, which may be wide in both the thickness direction and the height direction, may be formed inside the first cell 64. The first space 64a may make up a portion of the passage 62 of the measurement container 60.

One end side of the first cell 64 may include a cylindrically shaped first cell side connecting portion 65a to which the upstream side tube 22a may be connected, and a first cell side tapered portion 65b (i.e., an end side tapered portion) that gradually narrows from the cubic shaped main body portion toward the first cell side connecting portion 65a (i.e., the upstream side tube 22a). The first space 64a of the first cell 64 also exhibits a tapered shape on the inner side of the first cell side tapered portion 65b.

The second cell 66 may be formed so as to possess a flow path cross-sectional area and volume smaller than that of the first cell 64. For example, the flow path cross-sectional area of the second cell 66 may be set within the range of approximately one-third to two-thirds of the flow path cross-sectional area of the first cell 64. The second cell 66 may exhibit a substantially square-like shape as viewed in cross-section perpendicular to the axial direction of the measurement container 60, and the thickness T2 thereof along the direction of the arrow B shown in FIG. 3C may be shorter than the thickness T1 of the first cell 64, but on the other hand, the height H2 thereof along the direction of the arrow C shown in FIG. 3C may coincide with the height H1 of the first cell 64. Stated otherwise, the cross-sectional shape of the second cell 66 may be smaller only in the thickness direction with respect to the cross-sectional shape of the first cell 64.

In accordance with the shape of the container of the second cell 66, a second space 66a, which may be short in the thickness direction but wide in the height direction, may be disposed inside the second cell 66. The second space 66a may make up a portion of the passage 62 of the measurement container 60.

Another end side of the second cell 66 may include a cylindrically shaped second cell side connecting portion 67a to which the downstream side tube 22b may be connected, and a second cell side tapered portion 67b (an end side tapered portion) that gradually narrows from the cubic shaped main body portion toward the second cell side connecting portion 67a (the downstream side tube 22b). The second space 66a of the second cell 66 may also exhibit a tapered shape on the inner side of the second cell side tapered portion 67b.

The first cell 64 and the second cell 66 may be made continuous with each other via a flow path transitioning section 68 at an intermediate position in the axial direction of the measurement container 60. A pair of inclined wall portions 69 constituting the flow path transitioning section 68 may be inclined in the thickness direction of the measurement container 60 so as to approach toward each other from the first cell 64 toward the second cell 66. Stated otherwise, a thickness (not illustrated) of the flow path transitioning section 68 may gradually change between a thickness T1 and a thickness T2 of a pair of the first cell 64 and the second cell 66. Moreover, a height (not illustrated) of the flow path transitioning section 68 may coincide with a height H1 of the first cell 64 and a height H2 of the second cell 66.

In accordance with the shape of the flow path transitioning section 68, a transition space 68a that becomes narrower from the side of the first cell 64 toward the side of the second cell 66 may be provided in the interior of the flow path transitioning section 68. The transition space 68a may make up a portion of the passage 62 of the measurement container 60.

Figure 4:
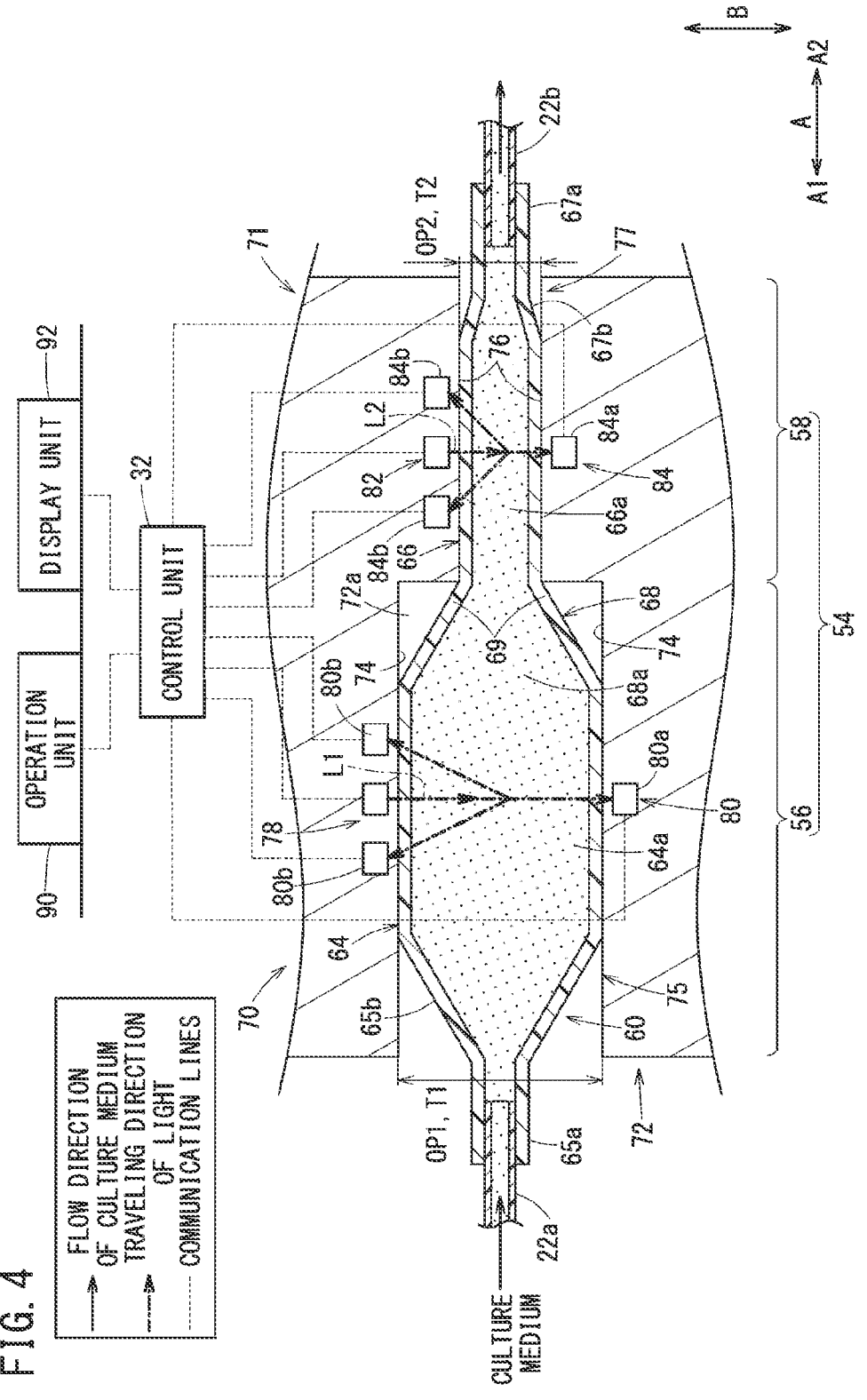
FIG. 4 is a partial cross-sectional view illustrating the example optical measurement unit of FIGS. 3A-3C at a time that the culture medium is flowing therethrough.

Corresponding to the above-described measurement container 60, the first measurement structure 70 and the second measurement structure 71 may be equipped with a series of holders 72, which as shown in FIG. 4, may sandwich the measurement container 60 therebetween in the thickness direction. The holders 72 may include an arrangement space 72a that extends along the direction of the arrow A. In order to expose the measurement container 60 (or the tubes 22 connected to the measurement container the 60), arrangement space 72a may be open at both ends of the holders 72 in the direction of the arrow A.

The holders 72 may include a pair of first retaining walls 74 that make up the first measurement structure 70 and retain the first cell 64, and a pair of second retaining walls 76 that make up the second measurement structure 71 and retain the second cell 66.

The pair of first retaining walls 74 may be wall portions erected in the thickness direction of the arrangement space 72a in the first measurement structure 70. An interval between the pair of first retaining walls 74 may coincide with the thickness T1 of the first cell 64. Therefore, in a state in which the first cell 64 may be arranged, the pair of first retaining walls 74 may sandwich the first cell 64 with an appropriate frictional force. In the first measurement unit 56, by the pair of first retaining walls 74, and the first cell 64 that may be arranged between the pair of first retaining walls 74, a first optical path section 75 may be formed through which the culture medium flows, and through which the first measurement light L1 may be transmitted.

The pair of second retaining walls 76 may be wall portions erected in the thickness direction of the arrangement space 72a in the second measurement structure 71. An interval between the pair of second retaining walls 76 may coincide with the thickness T2 of the second cell 66. Therefore, in a state in which the second cell 66 may be arranged, the pair of second retaining walls 76 may sandwich the second cell 66 with appropriate an frictional force. In the second measurement unit 58, by the pair of second retaining walls 76, and the second cell 66 that may be arranged between the pair of second retaining walls 76, a second optical path section 77 may be formed through which the culture medium flows, and through which the second measurement light L2 may be transmitted.

In addition, the first measurement structure 70 may include a first light emitting unit 78 that emits the first measurement light L1 toward the first cell 64, and a first light receiving unit 80 that receives the light from the first cell 64.

The first light emitting unit 78 may be disposed on one of the pair of first retaining walls 74 and may face toward the arrangement space 72a via a non-illustrated lens. The first light emitting unit 78 may emit the first measurement light L1 having a wavelength, for example, of greater than or equal to 660 nm, and preferably, greater than or equal to 860 nm. The first light emitting unit 78 may include one or more light emitting elements, such as an LED, an organic EL, an inorganic EL, an LD, and/or the like.

The first light receiving unit 80 may be configured to include at least one transmitted light element 80a for receiving transmitted light, and at least one scattered light element 80b for receiving scattered light. The transmitted light element 80a may be disposed on the first retaining wall 74 that directly faces toward the first light emitting unit 78 with the arrangement space 72a interposed therebetween. The scattered light element 80b may be disposed, for example, on the first retaining wall 74 on the same side as the first light emitting unit 78. The transmitted light element 80a and the scattered light element 80b may be constituted from a PD, a CMOS, and/or the like.

Similarly, the second measurement structure 71 may include a second light emitting unit 82 that emits the second measurement light L2 toward the second cell 66, and a second light receiving unit 84 that receives the light from the second cell 66.

The second light emitting unit 82 may include the same type of light emitting element as the first light emitting unit 78, may be disposed on one of the pair of second retaining walls 76, and may face toward the arrangement space 72a via a non-illustrated lens. The second light emitting unit 82 may emit the second measurement light L2 having a wavelength, for example, of greater than or equal to 660 nm, and preferably, greater than or equal to 860 nm. The wavelength of the second measurement light L2 may be the same as or different from the wavelength of the first measurement light L1.

The second light receiving unit 84, in the same manner as the first light receiving unit 80, may be configured to include at least one transmitted light element 84a for receiving transmitted light, and at least one scattered light element 84b for receiving scattered light. The transmitted light element 84a may be disposed on the second retaining wall 76 that directly faces toward the second light emitting unit 82 with the arrangement space 72a interposed therebetween. The scattered light element 84b may be disposed, for example, on the second retaining wall 76 on the same side as the second light emitting unit 82.

More specifically, the optical measurement unit 54 may employ a transmitted light and scattered light method in which the transmitted light of the first cell 64 and the second cell 66 (e.g., the light absorbed by the cells contained in the culture medium) and the scattered light of the first cell 64 and the second cell 66 (e.g., the light reflected by the cells contained in the culture medium) may be received and measurement thereof may be carried out. Moreover, the optical measurement unit 54 is not limited to using such a transmitted light and scattered light method and may adopt a transmitted light method in which only the respective transmitted lights of the first cell 64 and the second cell 66 may be received and measurement thereof is carried out. Alternatively, a scattered light method may be adopted in which only the respective scattered lights of the first cell 64 and the second cell 66 are received and measurement thereof may be carried out.

The first measurement structure 70 having the aforementioned configuration emits the first measurement light L1 with respect to the first cell 64 in the arranged state, and receives the transmitted light and the scattered light of the first cell 64. Accordingly, in the first optical path section 75, a first optical path length OP1 along the direction in which the first measurement light L1 travels may be defined by the distance between the pair of first retaining walls 74. T first optical path length OP1 coincides with the thickness T1 of the first cell 64 that may be sandwiched between the pair of first retaining walls 74.

Further, the second measurement structure 71 may emit the second measurement light L2 with respect to the second cell 66 in the arranged state, and may receive the transmitted light and the scattered light of the second cell 66. Accordingly, in the second optical path section 77, a second optical path length OP2 along the direction in which the second measurement light L2 travels may be defined by the distance between the pair of second retaining walls 76. The second optical path length OP2 may coincide with the thickness T2 of the second cell 66 that may be sandwiched between the pair of second retaining walls 76.

In addition, in the optical measurement unit 54, the first optical path length OP1 of the first optical path section 75 may be set to be longer than the second optical path length OP2 of the second optical path section 77 (i.e., OP1>OP2). The length of the first optical path length OP1 may be set within a range, for example, of 6 mm to 20 mm. The length of the second optical path length OP2 may be set within a range, for example, of 0.5 mm to 3 mm. Stated otherwise, the length of the first optical path length OP1 preferably resides within a range of 2 to 40 times that of the second optical path length OP2.

In addition, the first measurement unit 56 and the second measurement unit 58 may be set in a manner so that a measurement range of the first light receiving unit 80 that receives the transmitted light or the scattered light of the first measurement light L1, and a measurement range of the second light receiving unit 84 that receives the transmitted light or the scattered light of the second measurement light L2 differ from one another. More specifically, the first light receiving unit 80 which may be disposed in the longer first optical path length OP1 may correspond to a state in which the number of cells contained in the culture medium may be small (e.g., a small number of cells: a state of low concentration: a state of low turbidity). For example, the measurement range of the number of cells of the first light receiving unit 80 may be set to on the order of $10^5$ to $10^7$ cells/mL. On the other hand, the second light receiving unit 84 which may be disposed in the shorter second optical path length OP2 may correspond to a state in which the number of cells contained in the culture medium is large (e.g., a large number of cells: a state of high concentration: a state of high turbidity). For example, the measurement range of the number of cells of the second light receiving unit 84 may be set to on the order of 106 to $10^8$ cells/mL. In addition, in the cell culturing system 10, a first measurement result of the first light receiving unit 80 at a time of low concentration when the number of cells is small, and a second measurement result of the second light receiving unit 84 at a time of high concentration when the number of cells is large are used. Consequently, in relation to the optical measurement unit 54 as a whole, the measurement range of the number of cells may be made sufficiently wide. Moreover, three or more of the measurement units of the optical measurement unit 54 may be provided, and in such a case, the measurement ranges thereof may be set so as to differ in a stepwise manner.

Further, in the optical measurement unit 54, the first measurement light L1 of the first light emitting unit 78 and the second measurement light L2 of the second light emitting unit 82 may be emitted in different emission states (intensity, wavelength, or the like). More specifically, in order to measure a low concentration, the first light emitting unit 78 may emit the first measurement light L1 with a weak intensity. In accordance therewith, the first measurement unit 56 may be capable of irradiating the culture medium and the cells with the first measurement light L1 having an appropriate intensity. On the other hand, in order to measure a high concentration, the second light emitting unit 82 may emit the second measurement light L2 with a stronger intensity than the first measurement light L1. In accordance therewith, the second measurement unit 58 may be capable of irradiating the culture medium and the cells with the second measurement light L2 having an appropriate intensity.

The control unit 32 of the flow path control mechanism 24 may be constituted by a computer including at least one processor, a memory, and an input/output interface. The control unit 32 may be connected to an operation unit 90 and a display unit 92 provided in the flow path control mechanism 24, and based on operations of the operation unit 90 made by the user, sets an operating content of the flow path control mechanism 24, and further, displays the operating content or errors and the like on the display unit 92.

In addition, the control unit 32, by periodically controlling the optical measurement unit 54 and receiving the measurement result of the optical measurement unit 54, may calculate the number of cells cultured inside the reactor 12. For example, in the optical measurement, in accordance with the transmitted light and scattered light method, the control unit 32 may calculate the turbidity of the culture medium on the basis of a percentage between the detected values of the transmitted light elements 80a and 84a and the detected values of the scattered light elements 80b and 84b. Furthermore, the control unit 32 may possess in advance non-illustrated map information or a function indicative of the relationship between the turbidity of the culture medium and the number of cells in the reactor 12 and may calculate the number of cells in the reactor 12 from the calculated turbidity of the culture medium. The control unit 32 may display the calculated number of cells on the display unit 92.

When calculating the number of cells, the control unit 32 may selectively use the first measurement result of the first measurement unit 56 and the second measurement result of the second measurement unit 58. For example, when cell culturing is initiated, the number of cells contained within the culture medium may be small, and the culture medium exhibits a low concentration (low turbidity). Therefore, the control unit 32 may calculate the number of cells based on the first measurement result of the first measurement unit 56 having a measurement range of low concentration. At this time, the control unit 32 may or may not execute the measurement by using the second measurement unit 58. In the case that the measurement is performed by the second measurement unit 58, the control unit 32 may use the second measurement result thereof and thereby correct the first measurement result.

When the number of cells increases during cell culturing, in the measurement range of the first measurement unit 56, the measurement error of the number of cells may become large. Therefore, when the control unit 32 determines that the number of cells (the turbidity) has reached a value of greater than or equal to a non-illustrated switching threshold value that was set in advance, the control unit 32 may switch from using the first measurement result of the first measurement unit 56 to using the second measurement result of the second measurement unit 58. Moreover, switching between the first measurement result and the second measurement result is not limited to using the calculated number of cells, and may be performed, for example, on the basis of a predetermined culturing period having elapsed. Such a predetermined period may be configured to vary depending on a supplied amount of the culture medium and a supply rate or the like.

After undergoing such switching, the control unit 32 may calculate the number of cells based on the second measurement result of the second measurement unit 58 having a measurement range of high concentration (e.g., high turbidity). At this time, the control unit 32 may or may not execute the measurement by using the first measurement unit 56. In the instance where that the measurement is performed by the first measurement unit 56, the control unit 32 may use the first measurement result thereof and thereby correct the second measurement result.

As shown in FIG. 1, the operator of the cell culturing system 10, prior to execution of the culturing process, may place the culture medium storage unit 14, the plurality of medical bags 18, and the waste liquid unit 20 at positions in proximity to the outer side of the enclosure 26 of the flow path control mechanism 24. Further, the operator appropriately may set inside the enclosure 26 portions of the plurality of tubes 22 that constitute the reactor 12 and the flow path 16. Consequently, the flow path 16 shown in FIG. 2 may be constructed between the culture medium storage unit 14 and the reactor 12. Further, in the cell culturing system 10, as shown in FIGS. 3A and 4, at the time of being set, the measurement container 60 may be retained in the holders 72 of the flow path control mechanism 24.

After having been set as described above, in the culturing system 10, a priming step, a culture medium replacement step, a seeding step, a culturing step, a stripping step, and/or a collecting step may be sequentially performed. In the priming step, the cleaning solution which may be stored in the cleaning solution bag 18B may be supplied through the flow path 16 to the reactor 12, and air may be evacuated from the reactor 12 and the flow path 16. In the culture medium replacement step, the culture medium may be supplied from the culture medium storage unit 14 to the reactor 12 through the flow path 16 for which priming has been completed, and the interior and the exterior of the hollow fibers 34 may be filled with the culture medium. In the seeding step, the cell solution which may be stored in the cell solution bag 18A may be supplied to the interior of the hollow fibers 34 of the reactor 12 through the IC route 42, and the cells may be seeded on the inner peripheral surfaces of the hollow fibers 34.

Figure 2:
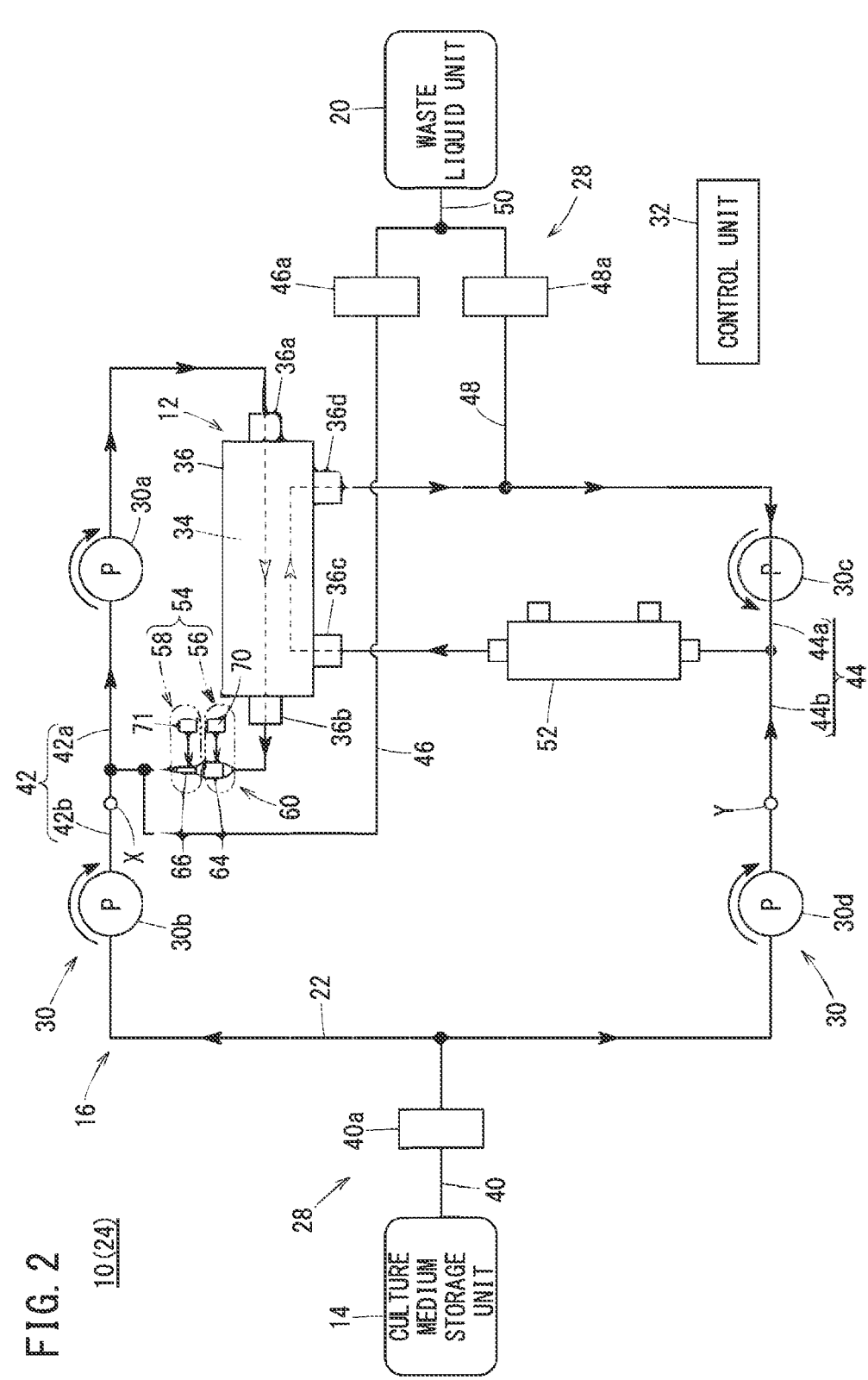
FIG. 2 is a circuit diagram illustrating an example flow path and an example flow path control mechanism between a culture medium storage unit and a reactor for use with the example cell culturing system illustrated in FIG. 1.

In addition, as shown in FIG. 2, in the culturing step, while passing through both the IC route 42 and the EC route 44, the cell culturing system 10 may supply the culture medium from the culture medium storage unit 14 into the hollow fibers 34, and culturing of the cells may take place inside the hollow fibers 34. At this time, oxygen may be supplied to the culture medium by the gas exchanger 52, and carbon dioxide may be discharged from the culture medium. The culturing step may be carried out for a longer period of time (for example, over several days) in comparison with the other steps, whereby the cells gradually propagate on the inner peripheral surfaces of the hollow fibers 34. Moreover, the cell culturing system 10 may be configured to supply the culture medium to the reactor 12 via the EC route 44, without passing through the IC supply circuit 42b. The culture medium, which has flowed through the EC route 44 and flowed into the reactor 12, may be supplied to the cells by way of seeping from the outer side to the inner side of the hollow fibers 34.

In the culturing step, the culture medium may flow into the passage 62 of the measurement container 60 from the upstream side tube 22a. The culture medium may pass through the first cell side tapered portion 65b whose flow path cross-sectional area gradually becomes larger, and may move into the main body portion of the first cell 64. The first measurement unit 56 may carry out the optical measurement in the main body portion of the first cell 64.

Furthermore, the culture medium may move from the first cell 64 toward the transition space 68a of the flow path transitioning section 68, may be gently gathered in the transition space 68a, and may then move from the transition space 68a into the main body portion of the second cell 66. The second measurement unit 58 may carry out the optical measurement in the main body portion of the second cell 66. Then, the culture medium may pass from the second cell 66 through the second cell side tapered portion 67b whose flow path cross-sectional area gradually becomes smaller, and may flow out into the downstream side tube 22b.

More specifically, although the measurement container 60 includes the first cell 64 and the second cell 66 whose flow path cross-sectional areas gradually become smaller, due to the end side tapered portions (e.g., the first cell side tapered portion 65b and the second cell side tapered portion 67b) and the flow path transitioning section 68, the culture medium may be allowed to flow while turbulence therein is suppressed. The optical measurement unit 54 may perform optical measurements on the culture medium that may undergo a laminar flow in the first space 64a of the first cell 64 and the second space 66a of the second cell 66, whereby the measurement accuracy is improved.

Figure 5:
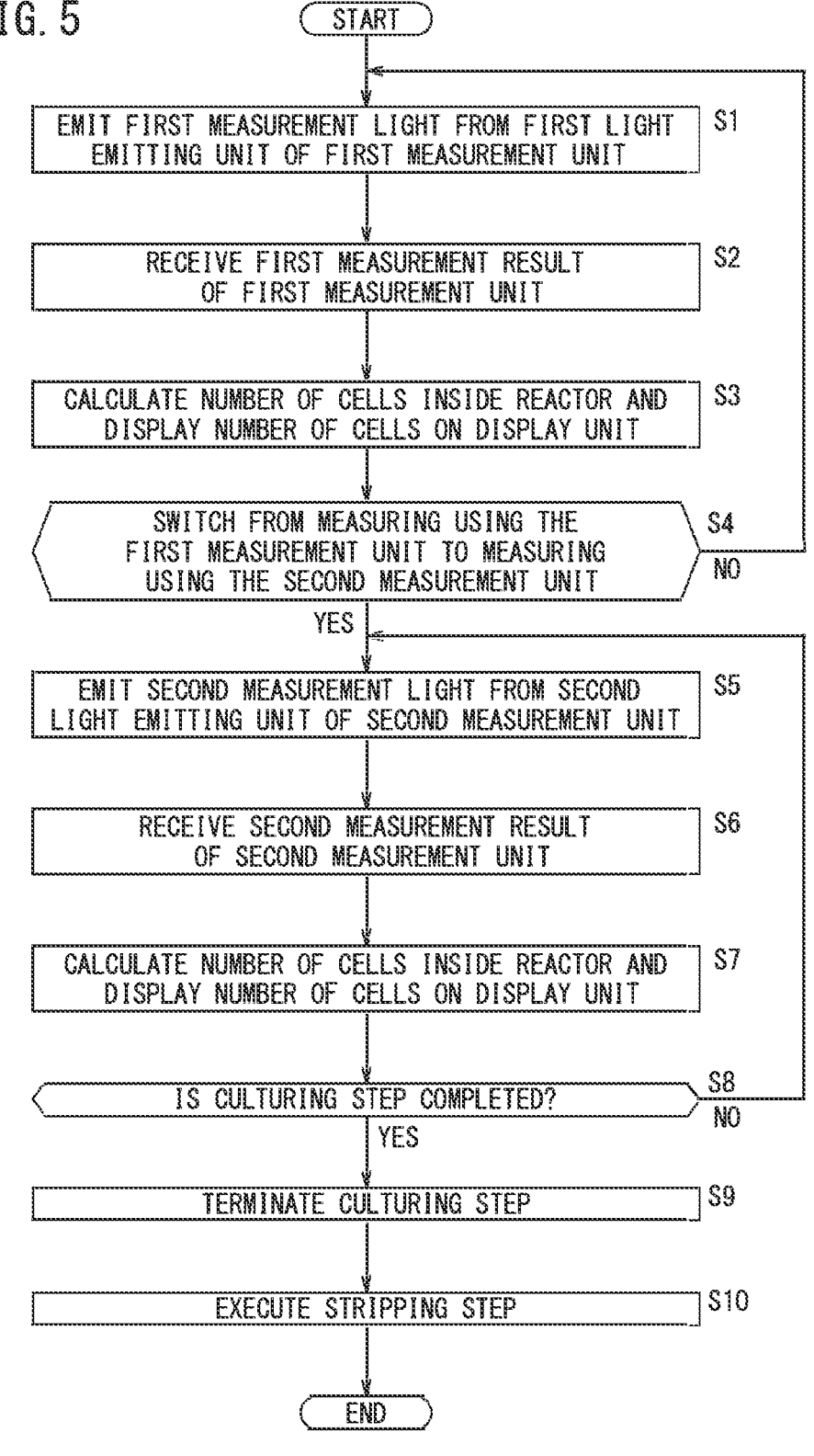
FIG. 5 is a flowchart illustrating operations of an example control unit for use with the example cell culturing system illustrated in FIG. 1.

In the culturing step and the stripping step, following along the flow of the process shown in FIG. 5, the control unit 32 of the flow path control mechanism 24 may monitor and control the state of the culture medium based on the measurements performed by the optical measurement unit 54. More specifically, when the culturing step is initiated, in order to measure the culture medium of a low concentration, at first, the control unit 32 may emit the first measurement light L1 from the first light emitting unit 78 of the first measurement unit 56 (i.e., step S1). Consequently, the first measurement light L1 may travel through the first optical path length OP1 of the first optical path section 75, and at this time, may impinge on the cells inside the first cell 64, and may be absorbed or scattered thereby.

Therefore, the first light receiving unit 80 of the first measurement unit 56 may receive the transmitted light and the scattered light from the first cell 64 and may transmit the first measurement result which is the detected value thereof. The control unit 32 may receive the first measurement result of the first measurement unit 56 (i.e., step S2). Then, on the basis of the received first measurement result, the control unit 32 may calculate the number of cells inside the reactor 12 and may display the calculated number of cells on the display unit 92 (i.e., step S3). By confirming the number of cells displayed on the display unit 92, the operator may be capable of recognizing the state of the cell culture.

Further, the control unit 32 may compare the calculated number of cells with the stored switching threshold value and may determine whether or not to switch from performing measurement using the first measurement unit 56 to performing measurement using the second measurement unit 58 (i.e., step S4). In the case that the number of cells is less than the switching threshold value, the process may return to step S1 and the same process flow may continue. On the other hand, in the case that the number of cells is greater than or equal to the switching threshold value, the process may proceed to step S5.

In step S5, in order to measure the culture medium of a high concentration, at first, the control unit 32 may emit the second measurement light L2 from the second light emitting unit 82 of the second measurement unit 58. Consequently, the second measurement light L2 may travel through the second optical path length OP2 of the second optical path section 77, and at this time, may impinge on the cells inside the second cell 66, and may be absorbed or scattered thereby.

Therefore, the second light receiving unit 84 of the second measurement unit 58 may receive the transmitted light and the scattered light from the second cell 66, and may transmit the second measurement result which may be t the detected value thereof, whereupon the control unit 32 may receive the second measurement result (i.e., step S6). On the basis of the second measurement result, the control unit 32 may calculate the number of cells inside the reactor 12, and may display the calculated number of cells on the display unit 92 (i.e., step S7).

Furthermore, the control unit 32 may compare the calculated number of cells with a stored collection value, and may determine whether or not to terminate the culturing step (step S8). In the case that the number of cells is less than the collection value, the process may return to step S5 and the same process flow may continue. On the other hand, in the case that the number of cells is greater than or equal to the collection value, the culturing step may be terminated (i.e., step S9), and the process may automatically transition to the stripping step. When the number of cells is greater than or equal to the collection value, the control unit 32 may issue a notification to the user concerning execution of the stripping step, and the stripping step may be executed under the operation of the user.

In the stripping step, the control unit 32 may temporarily stop the culture medium from flowing into the reactor 12, may guide the stripping solution stored in the stripping solution bag 18C into the interior of the hollow fibers 34 of the reactor 12 via the IC route 42, and may strip off the propagated cells (i.e., step S10). Furthermore, in the collecting step after completion of the stripping step, the control unit 32 may supply the culture medium to the IC route 42, and may thereby allow the cells that were stripped off in the stripping step to flow out from the reactor 12, and be moved into a non-illustrated collection bag.

Due to the process flow described above, the cell culturing system 10 may be capable of monitoring, in real time and with high accuracy, the number of cells that are cultured in the reactor 12. Accordingly, the cell culturing system 10 may be capable of appropriately grasping the timing at which the cells should be collected from the reactor 12 and can satisfactorily accommodate a target number of cells in the collection bag.

The present invention is not limited to the above-described embodiment, and various modifications can be adopted therein in accordance with the essence and gist of the present invention. For example, in the above-described embodiment, although the measurement container 60 may be configured to allow the culture medium to flow sequentially in order from the first cell 64 to the second cell 66, the flow direction of the culture medium may be sequentially in order from the second cell 66 to the first cell 64. Further, for example, in the above-described embodiment, although the first measurement unit 56 and the second measurement unit 58 may be disposed at positions adjacent to each other, the first measurement unit 56 and the second measurement unit 58 may be disposed at positions separated away from each other. Accordingly, the first cell 64 and the second cell 66 of the measurement container 60 need not necessarily be provided in a serial continuous configuration but may be disposed at positions separated away from each other, for example, via the tubes 22.

Figure 6:
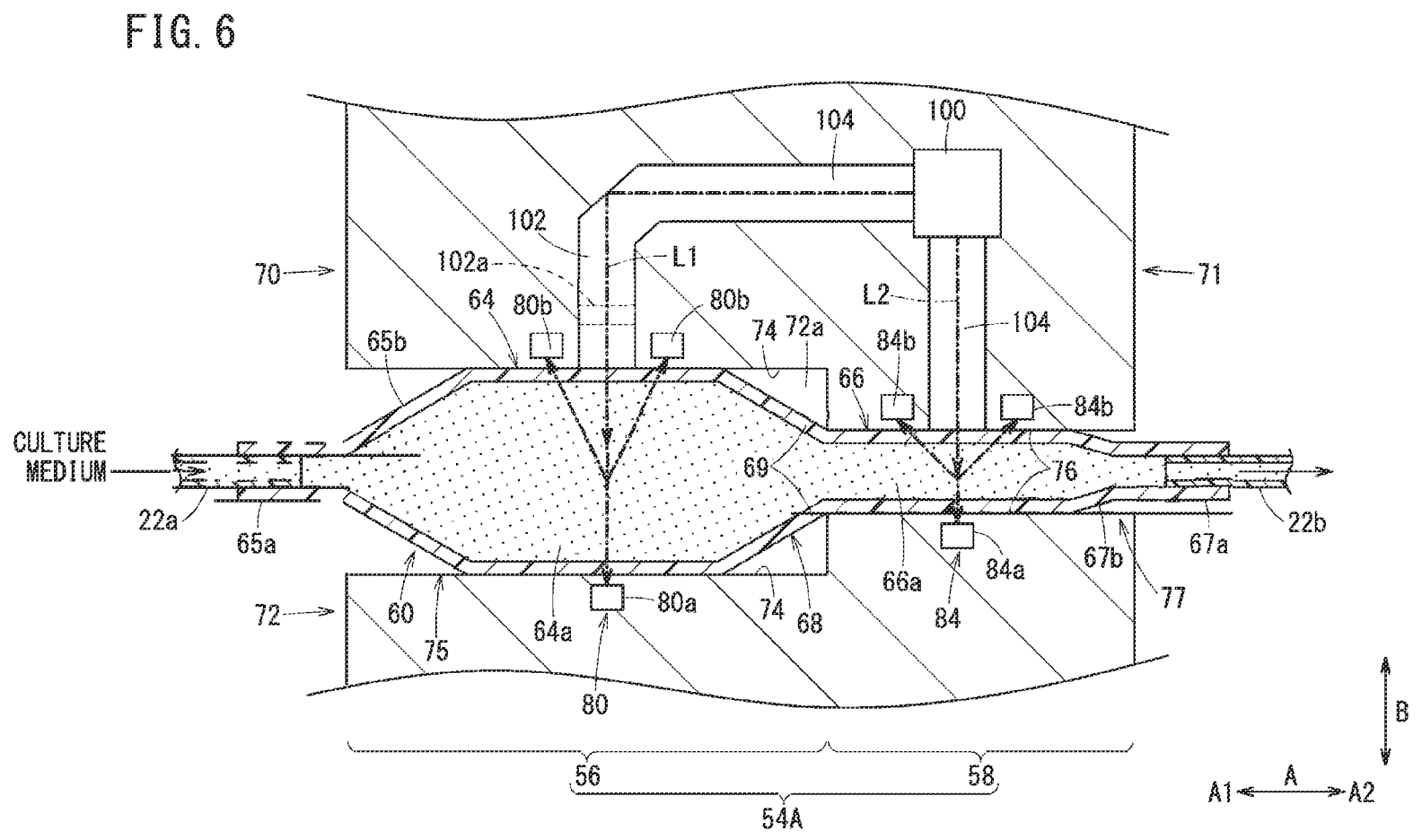

Furthermore, as in a modified example shown in FIG. 6, a configuration may be provided in which the first measurement unit 56 and the second measurement unit 58 of an optical measurement unit 54A share in common a light emitting unit 100 that emits the first measurement light L1 and the second measurement light L2. Even in such a configuration, the first light receiving unit 80 of the first measurement unit 56 and the second light receiving unit 84 of the second measurement unit 58 may be separately provided. Therefore, the measurement light emitted from the light emitting unit 100 may be received by the first light receiving unit 80 as the first measurement light L1 of the first measurement unit 56, together with being received by the second light receiving unit 84 as the second measurement light L2 of the second measurement unit 58.

By appropriately adjusting a first optical path 102 and a second optical path 104 from the light emitting unit 100 to the arrangement space 72a, the optical measurement unit 54A may alter the light intensity of the first measurement light L1 of the first measurement unit 56 and the light intensity of the second measurement light L2 of the second measurement unit 58. For example, as shown by the one-dot dashed lines in FIG. 6, by providing a lens 102a that reduces the light intensity in the first optical path 102, the light intensity of the first measurement light L1 may be made smaller than the light intensity of the second measurement light L2.

In at least one example embodiment, the reactor 12 may be configured to perform culturing of the cells based on the culture medium that flows therethrough. The optical measurement unit 54 or 54A disposed may be disposed in the flow path 16 downstream of the reactor 12 in the flow direction of the culture medium. The optical measurement unit 54 or 54A may be configured to irradiate the culture medium with the measurement light thereby optically measuring the state of the culture medium. The processing unit (e.g., the control unit 32) may be configured to process the measurement result of the optical measurement unit 54 or 54A. The optical measurement unit 54 or 54A may include the first measurement unit 56 and the second measurement unit 58 that are arranged at different positions in the flow direction of the culture medium. The first measurement unit 56 may include the first optical path section 75 through which the culture medium flows together with the first measurement light L1 being transmitted therein. The second measurement unit 58 may include the second optical path section 77 through which the culture medium flows together with the second measurement light L2 being transmitted therein. The first optical path length OP1 of the first optical path section 75 may be longer than the second optical path length OP2 of the second optical path section 77.

In at least one example embodiment, in the cell culturing system 10, due to the optical measurement unit 54 or 54A provided downstream of the reactor 12 in the flow direction of the culture medium in the flow path 16, it may be possible to continuously measure the number of cells in the reactor 12 in a state in which sterility is assured. Further, in at least one example embodiment, by the first optical path length OP1 of the first optical path section 75 being longer than the second optical path length OP2 of the second optical path section 77, the optical measurement unit 54 or 54A may enable the measurement ranges for the number of cells in the first measurement unit 56 and the number of cells in the second measurement unit 58 to be made different from each other. Accordingly, each of the first measurement unit 56 and the second measurement unit 58 may carry out highly accurate measurements within a narrow measurement range, and the optical measurement unit 54 or 54A may be capable of realizing a sufficient measurement accuracy as a whole.

In at least one example embodiment, the first cell 64 may be arranged in the first optical path section 75 and through which the culture medium flows, and the second cell 66 may be arranged in the second optical path section 77 and through which the culture medium flows. The flow path 16 may include the tubes 22 connected to the first cell 64 and the second cell 66. The first cell 64 and the second cell 66 may be configured to be harder than the tubes 22. Due to the first cell 64 and the second cell 66, which are hard and rigid, the cell culturing system 10 may enable the flow paths for the culture medium having the first optical path length OP1 and the second optical path length OP2 to be formed in a stable manner.

The first cell 64 and the second cell 66 may form a single container (e.g., the measurement container 60) in which the first cell 64 and the second cell 66 are continuous with each other along the flow direction of the culture medium. In accordance with this feature, the operator of the cell culturing system 10 can easily set the first cell 64 and the second cell 66 in the device.

Further, the container (e.g., the measurement container 60) may include the flow path transitioning section 68 between the first cell 64 and the second cell 66, which may have a gradually narrowing cross-sectional area of the flow path from the first cell 64 toward the second cell 66. Accordingly, even in a configuration in which the first cell 64 and the second cell 66 are continuous, the cell culturing system 10 may be capable of stabilizing the flowing state of the culture medium between the first cell 64 and the second cell 66.

Further, the end part of the first cell 64 and the end part of the second cell 66 to which the tubes 22 are connected may include end-side tapered portions (e.g., the first cell side tapered portion 65b and the second cell side tapered portion 67b) in which the cross-sectional area of the flow path gradually becomes smaller toward the tubes 22. Accordingly, when the culture medium flows in and flows out, the first cell 64 and the second cell 66 may become capable of suppressing turbulence in the culture medium. Thus, the cell culturing system 10 may be capable of further enhancing the accuracy of the optical measurements made with respect to the first cell 64 and the second cell 66.

In at least one example embodiment, when cell culturing is initiated, the processing unit (e.g., the control unit 32) may be configured to calculate the number of cells in the reactor 12 using the first measurement result of the first measurement unit 56, and in the case that the calculated number of cells is greater than or equal to the predetermined switching threshold value, may be configured to calculate the number of cells in the reactor 12 using the second measurement result of the second measurement unit 58. Accordingly, the cell culturing system 10 can satisfactorily follow along with changes in the number of cells in the reactor 12.

In at least one example embodiment, in the case that the number of cells has reached the predetermined collection value on the basis of the second measurement result, the processing unit (e.g., the control unit 32) may temporarily stop flowing of the culture medium to the reactor 12, and may supply to the reactor 12 a stripping solution for stripping off the cells from the reactor 12. Accordingly, when the cells cultured in the reactor 12 have reached the target number of cells, the cell culturing system 10 can smoothly collect the cells in the reactor 12.

In at least one example embodiment, the first measurement unit 56 may include the first light receiving unit 80 configured to receive the transmitted light of the first measurement light L1, together with receiving the scattered light in which the first measurement light L1 is scattered in the culture medium. The second measurement unit 58 may include the second light receiving unit 84 configured to receive the transmitted light of the second measurement light L2, together with receiving the scattered light in which the second measurement light L2 is scattered in the culture medium. Accordingly, the cell culturing system 10 may be capable of performing optical measurements by way of the transmitted light and scattered light method and can obtain the first measurement result and the second measurement result with higher accuracy.

In at least one example embodiment, the first measurement unit 56 and the second measurement unit 58 may share in common the light emitting unit 100 that emits the first measurement light L1 and the second measurement light L2. Accordingly, the optical measurement unit 54A may be capable of simplifying the structure and reducing costs.

In at least one example embodiment, the first measurement unit 56 may be configured to emit the first measurement light L1 with a light intensity that is weaker than the light intensity of the second measurement light L2 emitted by the second measurement unit 58. Accordingly, in the cell culturing system 10, it may be possible to measure the culture medium of a low concentration with higher accuracy in the first measurement unit 56, and further, it may be possible to measure the culture medium of a high concentration with higher accuracy in the second measurement unit 58.

The invention claimed is:

1. A cell culturing system comprising:
   a reactor configured to culture cells and to allow a culture medium to flow therethrough;
   an optical measurement unit disposed downstream of the reactor in a flow direction of the culture medium, the optical measurement unit configured to irradiate the culture medium with measurement light and thereby optically measure a state of the culture medium, the optical measurement unit including:
   a first measurement unit and a second measurement unit arranged at positions in the flow direction of the culture medium, wherein the first measurement unit includes a first optical path section configured to receive the culture medium and a first measurement light transmission, wherein the second measurement unit includes a second optical path section configured to receive the culture medium and a second measurement light transmission, the optical measurement unit; and
   a processing unit configured to process a measurement result of the optical measurement unit including;
   when cell culturing is initiated, to calculate number of cells in the reactor using a first measurement result of the first measurement unit;
   to compare the calculated number of cells to a predetermined switching threshold value; and
   when the calculated number of cells is greater than or equal to the predetermined switching threshold value, to calculate a revised number of cells in the reactor using a second measurement result of the second measurement unit.

2. The cell culturing system of claim 1, wherein the first measurement unit and the second measurement unit arranged at different positions in the flow direction of the culture medium.

3. The cell culturing system of claim 1, wherein the processing unit is further configured:
   to compare the calculated revised number of cells to a predetermined collection value; and
   to temporarily stop flowing of the culture medium to the reactor and supply to the reactor a stripping solution for stripping off the cells from the reactor.

4. The cell culturing system of claim 1, wherein the first measurement unit and the second measurement unit share a light emitting unit that is configured to emit both the first measurement light transmission and the second measurement light transmission.

5. The cell culturing system of claim 1, wherein the first measurement light transmission has a first light intensity and the second measurement light transmission as a second light intensity, the second light intensity being greater than the first light intensity.

6. The cell culturing system of claim 1, wherein a first optical path length along a first direction of the first measurement light transmission is longer than a second optical path length along a second direction of the second measurement light transmission.

7. The cell culturing system of claim 1, wherein the cell culturing system further includes:
   a first cell arranged in the first optical path section, and a second cell arranged in the second optical path section.

8. The cell culturing system of claim 7, wherein the first cell is connected to a tube and the first cell has a first modulus of elasticity that is greater than a second modulus of elasticity of the tube.

9. The cell culturing system of claim 8, wherein the first cell includes a first end part configured to connect to the tube, the first end part including an end-side tapered portion having a first end with a first cross-sectional area and configured to couple to the first cell, and a second end with a second cross-sectional area and configured to couple to the tube, the first cross-sectional area being greater than the second cross-sectional area.

10. The cell culturing system of claim 7, wherein the second cell is connected to a second tube and the second cell has a first modulus of elasticity that is greater than a second modulus of elasticity of the tube.

11. The cell culturing system of claim 10, wherein the second cell includes a second end part configured to connect to the tube, the second end part including an end-side tapered portion having a first end with a first cross-sectional area and configured to couple to the second cell, and a second end with a second cross-sectional area and configured to couple to the tube, the first cross-sectional area being greater than the second cross-sectional area.

12. The cell culturing system of claim 7, wherein the first cell and the second cell form a single container, wherein the first cell and the second cell are continuous with each other along the flow direction of the culture medium.

13. The cell culturing system of claim 12, wherein the single container includes a flow path transitioning section between the first cell and the second cell, the flow path transitioning section having a first end with a first cross-sectional area, and a second end with a second cross-sectional area, the first cross-sectional area being greater than the second cross-sectional area.

14. A cell culturing system comprising:

a flow path configured to receive culture medium;

a reactor in communication with the flow path and configured to culture cells;

an optical measurement unit in communication with the flow path downstream of the reactor in a flow direction of the culture medium, the optical measurement unit configured to irradiate the culture medium with measurement light and thereby optically measure a state of the culture medium, the optical measurement unit including:

a first measurement unit including a first optical path section configured to receive the culture medium and a first measurement light transmission, and a second measurement unit including a second optical path section configured to receive the culture medium and a second measurement light transmission, a first optical path length along a first direction of the first measurement light transmission being longer than a second optical path length along a second direction of the second measurement light transmission; and a processing unit configured to process a measurement result of the optical measurement unit including;

when cell culturing is initiated, to calculate number of cells in the reactor using a first measurement result of the first measurement unit;

to compare the calculated number of cells to a predetermined switching threshold value; and when the calculated number of cells is greater than or equal to the predetermined switching threshold value, to calculate a revised number of cells in the reactor using a second measurement result of the second measurement unit.

* * * * *